United States Patent [19]

Lang et al.

[11] Patent Number: 5,108,482
[45] Date of Patent: Apr. 28, 1992

[54] N-PHENYLPYRROLIDINES

[75] Inventors: Robert W. Lang, Pratteln; Urs Müller, Münchenstein, both of Switzerland

[73] Assignee: CIBA-GEIGY Corporation, Ardsley, N.Y.

[21] Appl. No.: 521,806

[22] Filed: May 10, 1990

[30] Foreign Application Priority Data

May 12, 1989 [CH] Switzerland ............... 1797/89

[51] Int. Cl.$^5$ .............. A01N 43/36; A01N 25/32; C07D 207/12; C07D 207/14
[52] U.S. Cl. ............................. 71/76; 71/88; 71/90; 71/92; 71/93; 71/94; 71/95; 71/77; 71/118; 548/531; 548/534; 544/141; 544/372; 546/208
[58] Field of Search .............. 548/534, 531; 71/93, 71/94, 95, 77, 88, 92, 76; 544/372, 141; 546/208

[56] References Cited

U.S. PATENT DOCUMENTS 3,136,620 6/1964 Bucha et al. ............................. 71/95
4,013,445 3/1977 Bellus et al. ............................. 71/76

OTHER PUBLICATIONS

Chemical Abstracts, vol. 109, No. 21, Abstract 190239Z, Nov. 24, 1988, p. 695.
Lowry et al. *An Introduction to Organic Chemistry*, 1951, p. 215.

Primary Examiner—C. Warren Ivy
Assistant Examiner—Amelia A. Owens
Attorney, Agent, or Firm—Edward McC. Roberts

[57] ABSTRACT

The 1-(3,5-bis-trifluoromethylphenyl)-2-thioxopyrrolidine-4-carboxylic acid derivatives of the formula I below are suitable for protecting crop plants against the phytotoxic action of herbicides and for regulating the plant growth.

The 1-(3,5-bis-trifluoromethylphenyl)-2-thioxopyrrolidine-4-carboxylic acid derivatives are those of the formula I

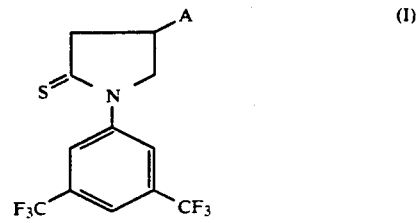

wherein A is $-COOR_1$, $-COSR_1$, $-COO^\ominus M^\oplus$, $-CONR_2R_3$ or $-COCl$; $R_1$ is hydrogen, $C_1-C_4$alkyl, $C_2-C_6$alkenyl or $C_2-C_6$alkynyl; $R_2$ and $R_3$ independently of one another are hydrogen, $C_1-C_4$alkyl or $C_3-C_7$cycloalkyl; or $R_2$ and $R_3$ together with the nitrogen atom to which they are bonded are a saturated 3- to 7-membered heterocycle which can contain an additional hetero atom selected from the group comprising O, N and S and which is unsubstituted or up to trisubstituted by $C_1$14 $C_4$alkyl; and $M^\oplus$ is the equivalent of an alkali metal cation or an alkaline earth metal cation or $HN^\oplus(R_2)_3$, and their isomers in optically pure or enriched form.

33 Claims, No Drawings

N-PHENYLPYRROLIDINES

The present invention relates to novel 1-(3,5-bis-trifluoromethylphenyl)-2-thioxopyrrolidine-4-carboxylic acid derivatives, to processes for their preparation, to agents containing these active substances, and to the use of these active substances and agents for protecting crop plants against the phytotoxic action of herbicides and for regulating plant growth.

It is known that when herbicides from the substance classes of the sulfonylureas and haloacetanilides are applied in effective doses they occasionally also damage the crop plants to a certain extent in addition to the weeds to be controlled. Overdoses are often applied unintentionally and randomly when margins overlap in strip spraying, be it by the action of wind or by wrongly estimating the width obtained by the sprayer. There may be climatic conditions or a type of soil which cause the amount of herbicide recommended for normal conditions to act as an overdose. It is also possible for the quality of the seed to play a role in the tolerance of the herbicide. To counter this problem, various substances have already been proposed which are capable of specifically antagonizing the damaging effect of the herbicide on the crop plant, i.e., to protect the crop plant without noticeably influencing the herbicidal action on the weeds to be controlled. In this context, it has emerged that the proposed antidotes often act very species-specific both with regard to the crop plants and to the herbicide and occasionally also as a function of the type of application, i.e., a certain antidote is often only suitable for one certain crop plant and some classes of herbicidal substances.

For example, British Patent Specification 1,277,557 describes the treatment of wheat and sorghum seeds or shoots with certain oxamic esters and amides to protect them from the action of "ALACHLOR" (N-methoxymethyl-N-chloroacetyl-2,6-diethylaniline). U.S. Pat. No. 4,618,331 discloses benzoxazine derivatives exerting a protective action against the herbicidal action of haloacetanilides and sulfonylureas. As a protection against sulfonylurea herbicides, EP-A-122.231 proposes benzoyl oxime ethers and EP-A-147,365 phenylglyoxylonitrile oxime, naphthalenedicarboxylic anhydride, a thiazolecarboxylic ester and dichloroacetamides as antidotes. According to German Offenlegungsschrift 2,402,983, it is furthermore possible to protect maize plants effectively against damage by chloroacetanilides by applying an N-disubstituted dichloroacetamide to the soil, as antidote. According to German Offenlegungsschriften 2,828,265 and 2,828,293, such compounds are also used as antidotes against herbicidal acetanilides.

U.S. Pat. No. 4,013,445 discloses 1-(bis-trifluoromethylphenyl)-2-oxopyrrolidine-4-carboxylic acid derivatives as herbicides and for regulating plant growth.

The use of 1-phenyl-2-oxopyrrolidine-4-carboxylic acids and of derivatives thereof which are unsubstituted on the phenyl ring or substituted by halogen atoms and/or a trifluoromethyl group, is known from French Patent Specification 1,363,615 and U.S. Pat. No. 3,136,620 as active substances for influencing plant growth.

It has now been found that, surprisingly, a group of N-phenylpyrrolidines is outstandingly suitable for protecting crop plants against the damaging action of sulfonylurea herbicides and chloroacetanilide herbicides.

These N-phenylpyrrolidines furthermore have very good plant-growth regulating properties.

The 1-(3,5-bis-trifluoromethylphenyl)-2-thioxopyrrolidine-4-carboxylic acid derivatives which are proposed according to the invention are those of the formula I

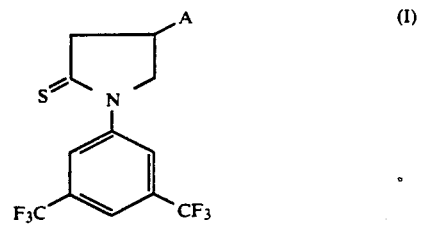

where A is $-COOR_1$, $-COSR_1$, $-COO^{\ominus}M^{\oplus}$, $-CONR_2R_3$ or $-COCl$; $R_1$ is hydrogen, $C_1$-$C_4$alkyl, $C_2$-$C_6$alkenyl or $C_2$-$C_6$alkynyl; $R_2$ and $R_3$ independently of one another are hydrogen, $C_1$-$C_4$alkyl or $C_3$-$C_7$cycloalkyl; or $R_2$ and $R_3$ together with the nitrogen atom to which they are bonded are a saturated 3- to 7-membered heterocycle which can contain an additional hetero atom selected from the group comprising O, N and S and which is unsubstituted or up to trisubstituted by $C_1$-$C_4$alkyl; and $M^{\oplus}$ is the equivalent of an alkali metal cation or an alkaline earth metal cation or $HN^{\oplus}(R_2)_3$, and their isomers in optically pure or enriched form.

Alkyl is understood as meaning straight-chain or branched alkyl, for example methyl, ethyl, n-propyl, i-propyl, n-butyl, i-butyl, sec-butyl or tert-butyl.

Alkenyl is understood as meaning straight-chain or branched alkenyl; for example: vinyl, allyl, 2-propenyl, methallyl, 3-butenyl, 2-butenyl, 3-pentenyl, 2-methyl-4-pentenyl and 3-hexenyl.

Alkynyl in the definitions is understood as meaning straight-chain or branched alkynyl; for example: propargyl, ethinyl, 2-propinyl, 3-butinyl, 2-methyl-3-pentinyl and 1,2-dimethyl-3-butinyl.

Cycloalkyl is, for example, cyclopropyl, dimethylcyclopropyl, cyclobutyl, cyclopentyl, methylcyclopentyl, cyclohexyl or cycloheptyl, but preferably cyclopropyl, cyclopentyl or cyclohexyl.

Particularly suitable cations $M^{\oplus}$ are those of alkali metals, for example lithium, sodium or potassium, and those of alkaline earth metals, for example magnesium or calcium. In particular, $M^{\oplus}$ is $HN^{\oplus}(R_2)_3$, where the substituents $R_2$ can be identical or different, or $M^{\oplus}$ is a cation of sodium or potassium.

When A is the amide radical $-CONR_2R_3$, the radicals mentioned below are particularly preferred: $-CONH_2$, $-CON(CH_3)_2$, $CON(C_2H_5)_2$,

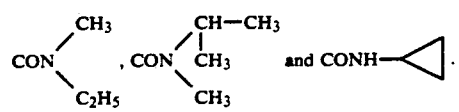

Examples of the heterocycles formed by the substituents $R_2$ and $R_3$ together with the nitrogen atom carrying them are pyrrolidine, piperazine, 2-methylpiperazine, piperidine and morpholine.

Preferred compounds of the formula I are those in which A is $-COOR_1$ or $-COO^{\ominus}M^{\oplus}$. Individual compounds from this group which are to be mentioned are:

1-(3,5-bis-trifluoromethylphenyl)-2-thioxopyrrolidine-4-carboxylic acid and methyl 1-(3,5-bis-trifluoromethylphenyl)-2-thioxopyrrolidine-4-carboxylate.

A particularly outstanding group of compounds of the formula I is formed by the optically active compounds of the formulae (R)-I and (S)-I

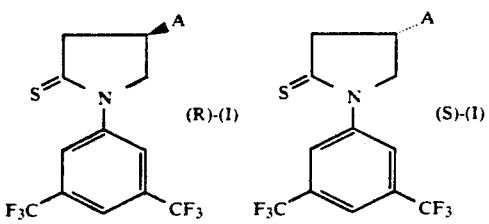

where A is as defined in formula I. Compounds from this group which are particularly noticeable by their good biological action are those in which A is —COOR₁ or —COO⊖M⊕. The following are to be mentioned as preferred individual compounds of the formulae (R)-I and (S)-I: 4-(R)-1-(3,5-bis-trifluoromethylphenyl)-2-thioxopyrrolidine-4-carboxylic acid, methyl 4-(R)-1-(3,5-bis-trifluoromethylphenyl)-2-thioxopyrrolidine-4-carboxylate, 4-(S)-1-(3,5-bis-trifluoromethylphenyl)-2-thioxopyrrolidine-4-carboxylic acid and methyl 4-(S)-1-(3,5-bis-trifluoromethylphenyl)-2-thioxopyrrolidine-4-carboxylate.

A compound of particularly outstanding mode of action is methyl 4-(R)-1-(bis-trifluoromethylphenyl)-2-thioxopyrrolidine-4-carboxylate.

The compounds of the formula I according to the invention can be prepared in a manner known per se by reacting, in the case of the racemic compounds of the formula I, a racemic 1-(3,5-bis-trifluoromethylphenyl)-2-oxopyrrolidine of the formula II

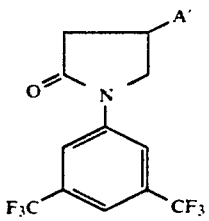

where A' is —COOR₁ and R₁ is C₁-C₄alkyl, which compound is known from U.S. Pat. No. 4,013,445, with a reagent capable of introducing the thioxo group to give the corresponding racemic 1-(3,5-bis-trifluoromethylphenyl)-2-thioxopyrrolidine-4-carboxylic esters of the formula Ia

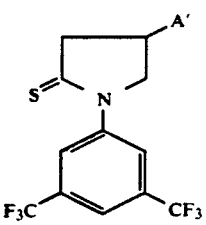

where A' is —COOR₁ and R₁ is C₁-C₄alkyl, and, if desired, subsequently converting these compounds in a manner known per se into the other derivatives of the formula I according to the definition, where A is as defined in formula I.

The optically active isomers of the formula I which are represented by the sub-formulae (R)-I and (S)-I are likewise a subject of the present invention. They can be prepared in a manner known per se by resolving a racemic 1-(3,5-bis-trifluoromethylphenyl)-2-oxopyrrolidine-4-carboxylic acid of the formula IIa

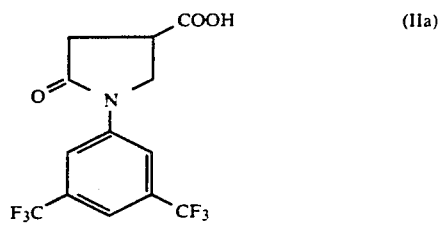

which is known from U.S. Pat. No. 4,013,445 by fractional crystallization, which is a method known per se, in the presence of a chiral auxiliary, for example an optically active base, in particular an optically active 1-phenylethylamine, into the optically active 4-(R)-(—)-1-(3,5-bis-trifluoromethylphenyl)-2-oxopyrrolidine-4-carboxylic acid of the formula (R)-IIa

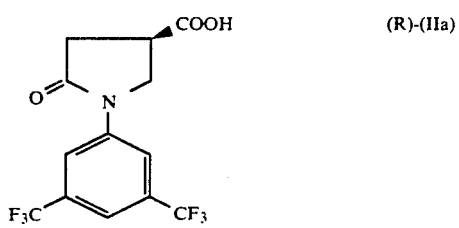

and the optically active 4-(S)-(+)-1-(3,5-bis-trifluoromethylphenyl)-2-oxopyrrolidine-4-carboxylic acid of the formula (S)-IIa

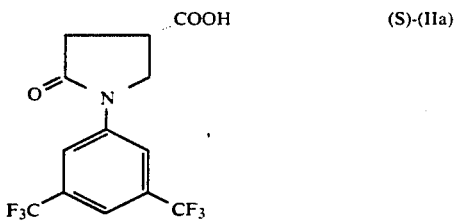

and, if desired, these isomers are converted in a manner known per se into the derivatives according to the definition of the formula (R)-IIb and (S)-IIb

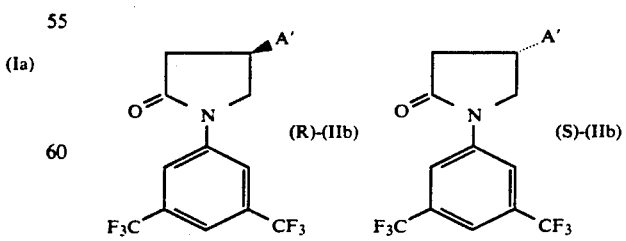

where A' is —COOR₁ and R₁ is C₁-C₄alkyl, so that by subsequent reaction with a reagent capable of introducing the thioxo group the corresponding compounds of the formulae (R)-Ia and (S)-Ia

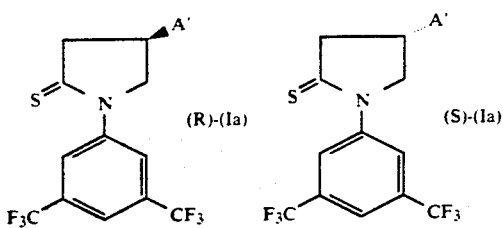

are obtained where A' is —COOR$_1$ and R$_1$ is C$_1$-C$_4$alkyl, and these compounds can, if desired, then be converted in a manner known per se into the other derivatives according to the definition. of the formulae (R)-I and (S)-I

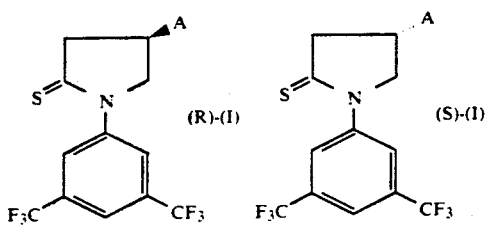

where A is as defined in formula I.

Reagents which are suitable for introducing the thioxo group are, for example, phosphorus pentasulfide and the arylthionophosphine sulfides derived therefrom. Such reagents are described in Tetrahedron 41, 5061–5087 (1985).

2,4-Bis-(4-methoxyphenyl)-1,3-dithia-2,4-diphosphetane 2,4-disulfide (Lawesson's reagent) has proved to be a particularly highly suitable reagent for introducing the thioxo group.

The intermediates of the formulae (R)-IIa, (S)-IIa, (S)-IIb and (S)-IIb are novel and likewise a subject of the present invention.

[4-(R)-(−)-1-(3,5-Bis-trifluoromethylphenyl)-2-oxopyrrolidine-4-carboxylic acid, of the formula (R)-IIa and [4-(S)-(+)-1-(3,5-bis-trifluoromethylphenyl)-2-oxopyrrolidine-4-carboxylic acid, of the formula (S)-IIa are converted into the other derivatives of the formulae (R)-IIb and (S)-IIb, respectively, according to the definition, in a manner known per se, for example:

by reacting the free carboxylic acids or the corresponding acid chlorides with alcohols R$_1$OH, or by esterifying the free carboxylic acid by generally known methods.

The racemic 1-(3,5-bis-trifluoromethylphenyl)-2-thioxopyrrolidine-4-carboxylic esters of the formula Ia and their optically active isomers of the formulae (R)-Ia and (S)-Ia are converted into the other derivatives of the formula I according to the definition in a manner known per se, for example:

to give the free carboxylic acids (A=—COOH) by acid hydrolysis of the esters of the formulae II, (R)-IIb or (S)-IIb.

to give the acid chlorides (A=—COCl) by reacting the free carboxylic acids with suitable chlorinating agents, for example thionyl chloride, oxalyl chloride, phosgene or PCl$_5$.

to give amides

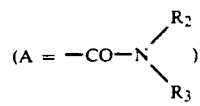

by reacting the acid esters, acid chlorides or free carboxylic acids with amines

to give thioesters (A=—COSR$_1$)
by reacting the acid chloride with mercaptans HSR$_1$;
to give alkali metal salts or alkaline earth metal salts
by reacting the free carboxylic acids with hydroxides, alcoholates or carbonates of alkali metals or alkaline earth metals, such as Na, K, Li, Ca and Mg hydroxide, sodium methylate, potassium methylate, sodium ethylate and potassium ethylate;
to give amine salts
by reacting the free carboxylic acid with amines N(R$_2$)$_3$.

The compounds of the formula I can be used for protecting crop plants against the damaging action of herbicides. Such compounds are also called "counteracting agent", "antidote" or "safener".

A counteracting agent or antidote of the formula I can be used for pretreating the seed of the crop plant (treatment of the seed or the cuttings) or can be introduced into the soil before or after sowing, depending on the intended use. It can be applied pre- or post-emergence either on its own or with the herbicide. The plant or the seed can therefore be treated with the antidote essentially independently of the point in time when the herbicide is applied. However, the plant can also be treated by simultaneously applying herbicide and counteracting agent (tank mix). Pre-emergence treatment includes treatment of the cropping area before sowing (ppi=pre-plant incorporation) and treatment of the cropping areas after sowing but before emergence of the plants.

The amounts of counteracting agent applied relative to the herbicide depend mostly on the type of application. In a field treatment in which herbicide and counteracting agent are applied either simultaneously (tank mix) or separately, the ratio of counteracting agent to herbicide is in the range of from 1:100 to 5:1. As a rule, the full protective action is achieved when the ratio of counteracting agent to herbicide is from 5:1 to 1:50. In seed treatment and similar targeted protective measures, however, much smaller amounts of counteracting agent are required compared with the amounts of herbicide later used per hectare of cropping area. In seed treatment, 0.1–10 g of counteracting agent are generally required per kg of seed. As a rule, the full protective action is already achieved with 0.1–5 g of counteracting agent per kg of seed. If the counteracting agent is to be applied shortly before sowing by means of seed soaking, it is advantageous to use solutions of the counteracting agent containing the active substance in a concentration of 1–10000 ppm. As a rule, the full protective action is achieved with concentrations of the counteracting agent of 100–1000 ppm.

As a rule. a substantial period of time elapses between protective measures such as seed treatment and treatment of cuttings with a counteracting agent of the formula I and any possible later field treatment with herbicides. Pretreated seeds and vegetative propagation stock can later come in contact with various chemicals in agriculture, horticulture and forestry. The invention therefore also relates to protective agents for crop plants which contain, as active substance, a counteracting agent of the formula I together with customary carriers. If desired, such agents can additionally contain those herbicides against whose effect the crop plant is to be protected. Propagation stock of crop plants, such as seeds, plantlets or cuttings, which is pretreated with active substances of the formula I is likewise a subject of the invention. The active substances of the formula I are particularly suitable for treating seeds of cereals and soya, preferably sorghum, maize and rice.

Examples of crop plants within the scope of the present invention are all cereal species, such as wheat, rye, barley and oats, and additionally mainly rice, cultured sorghums, maize and soya. Sorghum, maize and rice are preferred for protection by the active substances of the formula I against the action of sulfonylurea herbicides or chloroacetanilide herbicides.

A particularly good protective action against sulfonylurea herbicides and against chloroacetanilide herbicides is observed when the antidotes of the formula I are applied in maize, sorghum and rice. An excellent protective action is found in the case of chloroacetanilide herbicides in rice. A particularly favourable effect which must be emphasized is that of the compound of the formula I in which A is $-COOR_1$ or $-COO^\ominus M^\oplus$.

The compound methyl 4-(R)-1-(3,5-bis-trifluoromethylphenyl)-2-thioxopyrrolidine-4-carboxylate is especially suitable for protecting rice crops against the herbicidal action of N-chloroacetyl-N-(2-n-propoxyethyl)-2,6-diethylaniline.

A large number of sulfonylurea herbicides whose damaging action against crop plants can be compensated for with the aid of the N-acylsulfamoylphenylureas of the formula I have recently been disclosed. The following are to be mentioned as examples from amongst the large number of publications which deal with the disclosure of herbicidally-effective sulfonylurea derivatives: U.S. Pat. No. 4,127,405, and also the published European Patent Applications EP-A-7,687, EP-A-30,142, EP-A-44,807, EP-A-44,808, EP-A-51,466, EP-A-70,802, EP-A-84,020, EP-A-87,780, EP-A-102,925, EP-A-108,708, EP-A-120,814, EP-A-136,061, EP-A-184,385, EP-A-206,995 and EP-A-237,292.

Typical representatives of herbicidal sulfonylurea derivatives come under the formula III

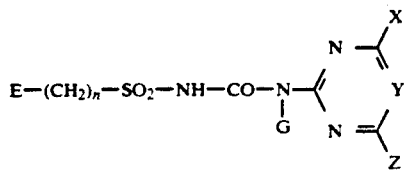

where E is a group

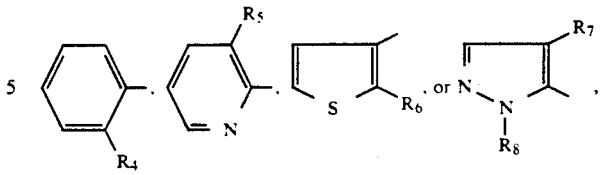

n is the number zero or one, G is hydrogen or methyl, X is methoxy, ethoxy, difluoromethoxy, methyl or chlorine, Y is CH or N, Z is methoxy, methyl, difluoromethoxy, cyclopropyl or methylamino. $R_4$ is $C_2-C_5$alkoxyalkoxy, $C_1-C_4$haloalkoxy, $C_1-C_4$haloalkylthio, $C_2-C_4$haloalkenyl, chlorine or $C_1-C_4$alkoxycarbonyl, $R_5$ is trifluoromethyl or di($C_1-C_4$alkyl)carbamoyl, $R_6$ is $C_1-C_4$alkoxycarbonyl, $R_7$ is $C_1-C_4$alkoxycarbonyl and $R_8$ is $C_1-C_4$alkyl.

The following individual herbicidal active substances come under the formula III:
N-(3-trifluoromethylpyridin-2-ylsulfonyl)-N'-(4,6-dimethoxypyrimidin-2-yl)-urea,
N-(3-dimethylcarbamoylpyridin-2-ylsulfonyl)-N'-(4,6-dimethoxypyrimidin-2-yl)-urea,
N-(1-methyl-4-ethoxycarbonylpyrazol-2-ylsulfonyl)-N'-(4,6-dimethoxypyrimidin-2-yl)-urea,
N-(2-methoxycarbonylthien-3-ylsulfonyl)-N'-(4-methoxy-6-methyl-1,3,5-triazin-2-yl)-urea,
N-(2-methoxycarbonylbenzylsulfonyl)-N'-(4,6-dimethoxypyrimidin-2-yl)-urea,
N-(2-methoxycarbonylphenylsulfonyl)-N'-(4,6-bis-difluoromethoxy-pyrimidin-2-yl)-urea,
N-(2-methoxycarbonylphenylsulfonyl)-N'-(4-ethoxy-6-methylamino-1,3,5-triazin-2-yl)-urea,
N-(2-methoxycarbonylphenylsulfonyl)-N'-(4-methoxy-6-methyl-1,3,5-triazin-2-yl)-urea,
N-(2-ethoxycarbonylphenylsulfonyl)-N'-(4-chloro-6-methoxypyrimidin-2-yl)-urea,
N-(2-methoxycarbonylphenylsulfonyl)-N'-(4-methoxy-6-methyl-1,3,5-triazin-2-yl)-N'-methylurea,
N-(2-methoxycarbonylphenylsulfonyl)-N'-(4,6-dimethoxypyrimidin-2-yl)-urea,
N-(2-chlorophenylsulfonyl)-N'-(4-methoxy-6-methyl-1,3,5-triazin-2-yl)-urea,
N-[2-(2-chloroethoxy)-phenylsulfonyl]-N'-(4-methoxy-6-methyl-1,3,5-triazin-2-yl)-urea and
N-[2-(2-methoxyethoxy)-phenylsulfonyl]-N'-(4,6-dimethoxy-1,3,5-triazin-2-yl)-urea.

Haloacetanilides whose damaging action against crop plants can be compensated for with the aid of N-phenylpyrrolidines of the formula I have likewise been disclosed in large numbers. Such haloacetanilides can be described by the general formula IV below:

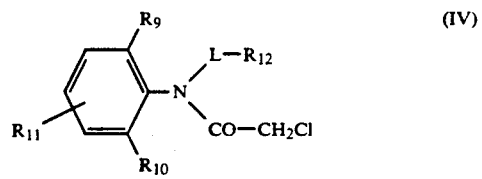

where L is a $C_1-C_4$alkylene bridge, $R_9$, $R_{10}$ and $R_{11}$ independently of one another are hydrogen, halogen, $C_1-C_4$alkyl, $C_1-C_4$alkoxy, $C_1-C_4$haloalkyl, $C_2-C_5$alkoxyalkyl or $C_2-C_5$alkylthioalkyl, and $R_{12}$ is $C_1-C_4$alkoxy, $-COOH$, $C_1-C_4$alkoxycarbonyl, $-CONH_2$, hydrogen, $C_1-C_4$alkylcarbamoyl, di-$C_1-C_4$alkylcarbamoyl, cyano, $C_1$-$C_4$alkylcarbonyl, substituted or unsubstituted benzoyl, substituted or unsubstituted furyl, substituted or unsubstituted thienyl, substituted or unsubstituted pyrrolyl, substituted or unsubstituted pyrazolyl, substituted or unsubstituted 1,3,4-oxadiazol-2-yl, substituted or unsubstituted 1,3,4-thiadiazol-2-yl, substituted or unsubstituted dioxolanyl, substituted or unsubstituted dioxanyl, substituted or unsubstituted 1,3,4-triazol-2-yl or substituted or unsubstituted tetrahydrofuryl.

The following herbicidal chloroacetanilide derivatives, in particular, come under the formula IV:

N-ethoxymethyl-N-chloroacetyl-2-ethyl-6-methylaniline,
N-chloroacetyl-N-methoxymethyl-2,6-diethylaniline,
N-chloroacetyl-N-(2-methoxyethyl)-2,6-dimethylaniline,
N-chloroacetyl-N-(2-n-propoxyethyl)-2,6-dimethylaniline,
N-chloroacetyl-N-(2-isopropoxyethyl)-2,6-dimethylaniline,
N-chloroacetyl-N-(2-methoxyethyl)-2-ethyl-6-methylaniline,
N-chloroacetyl-N-(methoxyethyl)-2,6-diethylaniline,
N-(2-ethoxyethyl)-N-chloracetyl-2-ethyl-6-methylaniline,
N-chloroacetyl-N-(2-methoxy-1-methylethyl)-2-methylaniline,
N-chloroacetyl-N-(2-methoxy-1-methylethyl)-2,6-dimethylaniline,
N-chloroacetyl-N-(2-methoxy-1-methylethyl)-2,6-diethylaniline,
N-chloroacetyl-N-(2-methoxy-1-methylethyl)-2-ethyl-6-methylaniline,
N-(2-ethoxyethyl)-N-chloroacetyl-2,6-diethylaniline,
N-chloroacetyl-N-(2-n-propoxyethyl)-2-ethyl-6-methylaniline,
N-chloroacetyl-N-(2-n-propoxyethyl)-2,6-diethylaniline,
N-chloroacetyl-N-(2-isopropoxyethyl)-2-ethyl-6-methylaniline,
N-ethoxycarbonylmethyl-N-chloroacetyl-2,6-dimethylaniline,
N-ethoxycarbonylmethyl-N-chloroacetyl-2,6-diethylaniline,
N-chloroacetyl-N-methoxycarbonylmethyl-2,6-dimethylaniline,
N-chloroacetyl-N-(2,2-diethoxyethyl)-2,6-dimethylaniline,
N-chloroacetyl-N-(2-methoxy-1-methylethyl)-2,3-dimethylaniline,
N-(2-ethoxyethyl)-N-chloroacetyl-2-methylaniline,
N-chloroacetyl-N-(2-methoxyethyl)-2-methylaniline,
N-chloroacetyl-N-(2-methoxy-2-methylethyl)-2,6-dimethylaniline,
N-(2-ethoxy-2-methylethyl)-N-chloroacetyl-2-ethyl-6-methylaniline,
N-chloroacetyl-N-(1-ethyl-1-methoxyethyl)-2,6-dimethylaniline,
N-chloroacetyl-N-(2-methoxyethyl)-2-methoxy-6-methylaniline,
N-n-butoxymethyl-N-chloroacetyl-2-tert-butylaniline,
N-chloroacetyl-N-(2-ethoxyethyl-2-methylethyl)-2,6-dimethylaniline,
N-chloroacetyl-N-(2-methoxyethyl)-2-chloro-6-methylaniline,
N-(2-ethoxyethyl)-N-chloroacetyl-2-chloro-6-methylaniline,
N-(2-ethoxyethyl)-N-chloroacetyl-2,3,6-trimethylaniline,
N-chloroacetyl-1-(2-methoxyethyl)-2,3,6-trimethylaniline,
N-chloroacetyl-N-cyanomethyl-2,6-dimethylaniline,
N-chloroacetyl-N-(1,3-dioxolan-2-ylmethyl)-2,6-dimethylaniline,
N-chloroacetyl-N-(1,3-dioxolan-2-ylmethyl)-2-ethyl-6-methylaniline,
N-chloroacetyl-N-(1,3-dioxan-2-ylmethyl)-2-ethyl-6-methylaniline,
N-chloroacetyl-N-(2-furylmethyl)-2,6-dimethylaniline,
N-chloroacetyl-N-(2-furylmethyl)-2-ethyl-6-methylaniline,
N-chloroacetyl-N-(2-tetrahydrofurylmethyl)-2,6-dimethylaniline,
N-chloroacetyl-N-(N,N-dimethylcarbamoylmethyl)-2,6-dimethylaniline,
N-(n-butoxymethyl)-N-chloroacetyl-2,6-diethylaniline,
N-(2-n-butoxyethyl)-N-chloroacetyl-2,6-diethylaniline,
N-chloroacetyl-N-(2-methoxy-1,2-dimethylethyl)-2,6-dimethylaniline,
N-chloroacetyl-N-isopropyl-2,3-dimethylaniline,
N-chloroacetyl-N-isopropyl-2-chloroaniline,
N-chloroacetyl-N-(1H-pyrazol-1-ylmethyl)-2,6-dimethylaniline,
N-chloroacetyl-N-(1H-pyrazol-1-ylmethyl)-2-ethyl-6-methylaniline,
N-chloroacetyl-N-(1H-1,2,4-triazol-1-ylmethyl)-2,6-dimethylaniline,
N-chloroacetyl-N-(1H-1,2,4-triazol-1-ylmethyl)-2,6-diethylaniline,
N-benzoylmethyl-N-chloroacetyl-2,6-diethylaniline,
N-benzoylmethyl-N-chloroacetyl-2-ethyl-6-methylaniline,
N-chloroacetyl-N-(5-methyl-1,3,4-oxadiazol-2-yl)-2,6-diethylaniline,
N-chloroacetyl-N-(5-methyl-1,3,4-oxadiazol-2-yl)-2-ethyl-6-methylaniline,
N-chloroacetyl-N-(5-methyl-1,3,4-oxadiazol-2-yl)-2-tert-butyl aniline,
N-chloroacetyl-N-(4-chlorobenzoylmethyl)-2,6-dimethylaniline and
N-chloroacetyl-N-(1-methyl-5-methylthio-1,3,4-triazol-2-ylmethyl)-2,6-diethylaniline.

The antidotes of the formula I are especially suitable for protecting crop plants against the herbicidal effects of the herbicides of the formulae III or IV.

Agrochemicals containing, besides the antidote of the formula I, a sulfonylurea herbicide or a chloroacetanilide herbicide in a combined formulation, are suitable for use as selective herbicides in crops.

Besides an antidote of the formula I, the herbicidal agents according to the invention preferably contain a sulfonylurea of the formula III or a chloroacetanilide of the formula IV.

Unless used in seed treatment, the amount of counteracting agent applied is between about 0.01 and about 5 parts by weight per part by weight of herbicide. In practice, the ideal ratio with regard to optimum effect in the specific crop plant is determined from case to case, i.e., depending on the type of herbicide used.

The invention also relates to a method for selectively controlling weeds in crops, in which method the crops, parts of crop plants, or cropping areas for crop plants, are treated with a herbicide and a compound of the formula I or with an agent containing this combination.

The agents containing the herbicide/antidote combination are likewise part of the present invention.

The weeds to be controlled can be monocotyledon and dicotyledon weeds.

The invention also relates to plant-growth regulating agents containing a novel active substance of the formula I, and to methods for inhibiting plant growth.

Plant growth regulators are substances which cause agronomically desired biochemical and/or physiological and/or morphological alterations in/on the plant.

The active substances contained in the agents according to the invention have various effects on the plant growth, depending on the point in time of application, the dosage, the type of application and the environmental conditions. For example, plant growth regulators of the formula I can inhibit the vegetative growth of plants. This type of action is interesting on lawns, in the production of ornamental plants, in orchards, on verges, on sports grounds and industrial terrain, but also in the targeted inhibition of secondary shoots, such as in tobacco. In arable farming, inhibition of the vegetative growth in cereals by means of thickened stems results in reduced lodging, and similar agronomical effects are achieved in oil seed rape, sunflowers, maize and other crop plants. Moreover, inhibition of the vegetative growth makes it possible to increase the number of plants per unit area. Another field of application of growth inhibitors is the selective control of groundcover plants in plantations or crops with substantial distances between the rows by powerful inhibition of growth without killing these ground-cover plants, which results in the elimination of competition with the main crop but agronomically positive effects, such as prevention of erosion, nitrogen fixation and loosening of the soil, are retained.

A method for inhibiting plant growth is taken to mean that man interferes with the natural development of the plant without altering, in the sense of a mutation, the life cycle of the plant which is determined by the genetic make-up. The method of growth regulation is applied at a point in time of development of the plant to be determined in the individual case. The active substances of the formula I can be applied before or after emergence of the plants, for example as early as in the seed stage, or to the seedlings, to roots, tubers, stalks, leaves, flowers or other parts of the plant. This can be effected for example by applying the active substance itself or in the form of an agent to the plants and/or by treating the culture substrate of the plant (soil).

It is preferred to employ the compounds of the formula I according to the invention for inhibiting the growth in dicotyledon crops by post-emergence application.

A series of methods and techniques is suitable for using the compound of the formula I or an agent containing it, for protecting crop plants against the damaging effects of herbicides and for regulating plant growth, for example the ones cited below:

i) Seed Treatment a) Seed treatment with an active substance formulated as a wettable powder, by shaking in a container until the active substance is uniformly distributed on the seed surface (dry seed treatment). For this purpose, about 0.1 to 2.0 g of active substance of the formula I are used per kg of seed (in the case of a 25% formulation: 0.4 g to 8.0 g of wettable powder).

b) Seed treatment with an emulsion concentrate of the active substance or with an aqueous solution of the active substance of the formula I formulated as a wettable powder, by method a) (wet seed treatment).

c) Treatment by immersing the seed in a liquor containing 10–1000 ppm of active substance of the formula I for 1 to 72 hours, followed, if desired, by drying seeds (seed soaking).

Seed treatment, or treatment of the pregerminated seedling, is naturally the preferred application method since the treatment with active substance is entirely directed on the target crop. As a rule, 6.0 g to 0.01 g, preferably 2.0 to 0.1 g, of active ingredient are used per kg of seed, it being possible to deviate in either direction from the limit concentrations indicated, depending on the particular method which also makes possible the addition of other active substances or micronutrients (repeated seed treatment).

ii) Application from a Tank Mix

A liquid composition of a mixture of counteracting agent and herbicide (mutual ratio between 100:1 and 1:100, preferably 10:1 and 1:10) is used, the amount of herbicide and safener applied being 0.001 to 10 kg per hectare. Such a tank mix is preferably applied before or after sowing, or incorporated into the soil at a depth of 5 to 10 cm, before sowing.

iii) Application in the Seed Furrow

After sowing, the counteracting agent is applied to the open seed furrow in the form of an emulsion concentrate, wettable powder or granules, and after the seed furrow has been covered, the herbicide is applied pre-emergence in the usual manner.

iv) Controlled Release of Active Substance

Mineral granule carriers or polymerized granules (urea/formaldehyde) are coated with a solution of active substance and allowed to dry. If desired, a coating can be applied (coated granules) which permits controlled release of the active substance over a certain period.

The compounds of the formula I are employed as they stand, or preferably as agents in conjunction with the auxiliaries conventionally used in formulations, and as such are processed by known methods to give, for example, emulsion concentrates, directly sprayable or dilutable solutions, dilute emulsions, wettable powders, soluble powders, dusts, granules and capsules, for example in polymeric substances. The method of application, such as spraying, atomization, dusting, scattering or watering, is chosen, as is the type of agent, according to the intended purpose and the prevailing conditions.

The formulations, i.e., the agents, preparations or compositions containing the active substance of the formula I and, if desired, a solid or liquid additive, are prepared in a known manner, for example by intimately mixing and/or grinding the active substances with extenders, for example with solvents, solid carriers, and, if desired, surface-active compounds (surfactants).

The following are suitable as solvents: aromatic hydrocarbons, preferably the fractions $C_8$ to $C_{12}$, for example xylene mixtures or substituted naphthalenes, phthalic esters, such as dibutyl phthalate or dioctyl phthalate, aliphatic hydrocarbons, such as cyclohexane or paraffins, alcohols and glycols as well as their ethers and esters, such as ethanol, ethylene glycol, ethylene glycol monomethyl ether or ethylene glycol monoethyl ether, ketones, such as cyclohexanone, strongly polar solvents, such as N-methyl-2-pyrrolidone, dimethyl sulfoxide or dimethylformamide, and epoxidized or unepoxidized vegetable oils, such as epoxidized coconut oil or soya oil; or water.

Examples of solid carriers which are generally used, for example for dusts and dispersible powders, are natural ground minerals, such as calcite, talc, kaolin, montmorillonite or attapulgite. To improve the physical properties, it is also possible to add highly-disperse silica or highly-disperse, absorptive polymers. Particulate, absorptive granule carriers are porous types, for example pumice, brick grit, sepiolite or bentonite, and examples of non-sorptive carrier materials are calcite or sand. Moreover, a large number of pregranulated materials of inorganic or organic nature, such as, in particular, dolomite or comminuted plant residues, can be used.

Suitable surface-active compounds are non-ionic, cationic and/or anionic surfactants having good emulsifying, dispersing and wetting properties, depending on the nature of the active substance of the formula I to be formulated. Surfactants are also understood as meaning mixtures of surfactants.

Anionic surfactants which are suitable can be either so-called water-soluble soaps or water-soluble synthetic surface-active compounds.

Soaps which may be mentioned are the alkali metal salts, alkaline earth metal salts or substituted or unsubstituted ammonium salts of higher fatty acids ($C_{10}$–$C_{22}$), for example the Na or K salts of oleic or stearic acid, or of natural mixtures of fatty acids which can be obtained from, for example, coconut or tallow oil. Mention must also be made of the fatty acid methyl-taurinates.

However, so-called synthetic surfactants are used more frequently, in particular fatty sulfonates, fatty sulfates, sulfonated benzimidazole derivatives or alkylarylsulfonates.

The fatty sulfates or fatty sulfonates are usually in the form of alkali metal salts, alkaline earth metal salts or substituted or unsubstituted ammonium salts and have an alkyl radical having 8 to 22 C atoms, alkyl also including the alkyl moiety of acyl radicals, for example the Na or Ca salt of ligninsulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives preferably contain 2 sulfonyl groups and a fatty acid radical having 8 to 22 C atoms. Examples of alkylarylsulfonates are the Na, Ca or triethanolamine salts of dodecylbenzenesulfonic acid, of dibutylnaphthalenesulfonic acid or of a naphthalenesulfonic acid/formaldehyde condensation product.

Other suitable compounds are appropriate phosphates, for example salts of the phosphoric ester of a p-nonylphenol/(4-14)-ethylene oxide adduct, or phospholipids.

Suitable non-ionic surfactants are mainly polyglycol ether derivatives of aliphatic or cycloaliphatic alcohols, saturated or unsaturated fatty acids and alkylphenols which can contain 3 to 10 glycol ether groups and 8 to 20 carbon atoms in the (aliphatic) hydrocarbon radical and 6 to 18 carbon atoms in the alkyl radical of the alkylphenols.

Other suitable non-ionic surfactants are the water-soluble polyethylene oxide adducts with polypropylene glycol, ethylenediaminopolypropylene glycol and alkylpolypropylene glycol which have 1 to 10 carbon atoms in the alkyl chain and contain 20 to 250 ethylene glycol ether groups and 10 to 100 propylene glycol ether groups, the abovementioned compounds generally containing 1 to 5 ethylene glycol units per propylene glycol unit.

Examples of non-ionic surfactants which may be mentioned are nonylphenolpolyethoxyethanols, castor oil polyethylene glycol ether, polypropylene/polyethylene oxide adducts, tributylphenoxypolyethoxyethanol, polyethylene glycol and octylphenoxypolyethoxyethanol.

Other suitable substances are fatty acid esters of polyoxyethylene sorbitan, such as polyoxyethylene sorbitan trioleate.

The cationic surfactants are mainly quaternary ammonium salts which contain at least one alkyl radical having 8 to 22 C atoms as N-substituents and lower, halogenated or unhalogenated alkyl, benzyl or lower hydroxyalkyl radicals as further substituents. The salts are preferably in the form of halides, methylsulfates or ethylsulfates, for example stearyltrimethylammonium chloride or benzyldi(2-chloroethyl)-ethylammonium bromide.

The surfactants conventionally used in the art of formulation are described, inter alia, in the following publications:

"Mc Cutcheon's Detergents and Emulsifiers Annual" MC Publishing Corp., Ridgewood, N.J., 1981;

H. Stache, "Tensid-Taschenbuch" [Surfactants Guide], 2nd edition, C. Hanser Verlag, Munich, Vienna, 1981;

M. and J. Ash. "Encyclopedia of Surfactants", Vol. I-III, Chemical Publishing Co., New York, 1980-1981.

As a rule, the agrochemical preparations contain 0.1 to 95%, in particular 0.1 to 80%, of active substance of the formula I, 1 to 99.9% of a solid or liquid additive and 0 to 25%, in particular 0.1 to 25%, of a surfactant.

Preferred formulations have particularly the following compositions: (% = percent by weight).

| Emulsifiable concentrate: | |
|---|---|
| Active ingredient: | 1 to 20%, preferred: 5 to 10% |
| Surface-active agent: | 5 to 30%, preferably 10 to 20% |
| Liquid carrier: | 50 to 94%, preferably 70 to 85% |
| Dusts: | |
| Active ingredient: | 0.1 to 10%, preferably 0.1 to 1% |
| Solid carrier: | 99.9 to 90%, preferably 99.9 to 99% |
| Suspension concentrates: | |
| Active ingredient: | 5 to 75%, preferably 10 to 50% |
| Water: | 94 to 24%, preferably 88 to 30% |
| Surface-active agent: | 1 to 40%, preferably 2 to 30% |
| Wettable powder: | |
| Active ingredient: | 0.5 to 90%, preferably 1 to 80% |
| Surface-active agent: | 0.5 to 20%, preferably 1 to 15% |
| Solid carrier: | 5 to 99%, preferably 15 to 90% |
| Granules: | |
| Active ingredient: | 0.5 to 30%, preferably 3 to 15% |
| Solid carrier: | 99.5 to 70%, preferably 97 to 85% |

While relatively concentrated agents are preferred as merchandise, the end user, as a rule, uses dilute agents. The use forms can be diluted down to 0.001% of active substance. As a rule, the application rates are 0.01 to 10 kg of active compound/ha, preferably 0.025 to 5 kg of active compound/ha.

The agents can also contain other additives, such as stabilizers, defoamers, viscosity regulators, binders, tackifiers as well as fertilizers or other active substances for achieving specific effects.

FORMULATION EXAMPLES

EXAMPLE F1: FORMULATION EXAMPLES OF ACTIVE SUBSTANCES OF THE FORMULA I (%=PERCENT BY WEIGHT)

| a) Wettable powders | a) | b) | c) |
|---|---|---|---|
| Active substance No. 1.01 | 20% | 50% | 0.5% |
| Na ligninsulfonate | 5% | 5% | 5% |
| Na lauryl sulfate | 3% | 5% | 5% |
| Na diisobutylnaphthalenesulfonate | — | 6% | 6% |
| Octylphenol polyethylene glycol ether (7-8 mol of EO) | — | 2% | 2% |
| Highly disperse silica | 5% | 27% | 27% |
| Kaolin | 67% | 10% | — |
| Sodium chloride | — | — | 59.5% |

The active substance is thoroughly mixed with the additives, and the mixture is ground thoroughly in a suitable mill. This gives wettable powders which can be diluted with water to give suspensions of any desired concentration.

| b) Emulsion concentrate | a) | b) |
|---|---|---|
| Active substance No. 1.02 | 10% | 1% |
| Octylphenol polyethylene glycol ether (4-5 mol of EO) | 3% | 3% |
| Ca dodecylbenzenesulfonate | 3% | 3% |
| Castor oil polyglycol ether (36 mol of EO) | 4% | 4% |
| Cyclohexanone | 30% | 10% |
| Xylene mixture | 50% | 79% |

Emulsions of any desired concentration can be prepared from this concentrate by dilution with water.

| c) Dusts | a) | b) |
|---|---|---|
| Active substance No. 1.02 | 0.1% | 1% |
| Talc | 99.9% | — |
| Kaolin | — | 99% |

Ready-to-use dusts are obtained by mixing the active substance with the carrier and grinding the mixture on a suitable mill.

| d) Extruder granules | a) | b) |
|---|---|---|
| Active substance No. 1.01 | 10% | 1% |
| Na ligninsulfonate | 2% | 2% |
| Carboxymethylcellulose | 1% | 1% |
| Kaolin | 87% | 96% |

The active substance is mixed with the additives, and the mixture is ground and moistened with water. This mixture is extruded and then dried in a stream of air.

| e) Coated granules | |
|---|---|
| Active substance No. 1.01 | 3% |
| Polyethylene glycol (MW 200) | 3% |
| Kaolin | 94% |

The kaolin is moistened with polyethylene glycol and uniformly coated in a mixer with the finely ground active substance. In this manner, dust-free coated granules are obtained.

| f) Suspension concentrate | a) | b) |
|---|---|---|
| Active substance No. 1.02 | 40% | 5% |
| Ethylene glycol | 10% | 10% |
| Nonylphenol polyethylene glycol ether (15 mol of EO) | 6% | 1% |
| Na ligninsulfonate | 10% | 5% |
| Carboxymethylcellulose | 1% | 1% |
| 37% aqueous formaldehyde solution | 0.2% | 0.2% |
| Silicone oil in the form of a 75% aqueous emulsion | 0.8% | 0.8% |
| Water | 32% | 77% |

The finely-ground active substance is mixed intimately with the additives. In this manner, a suspension concentrate is obtained from which suspensions of any desired concentration can be prepared by dilution with water.

| g) Salt solution | |
|---|---|
| Active substance No. 1.02 | 5% |
| Isopropylamine | 1% |
| Octylphenol polyethylene glycol ether (78 mol of EO) | 3% |
| Water | 91% |

PREPARATION EXAMPLES

The examples below demonstrate the preparation of some compounds according to the invention.

EXAMPLE H1

Preparation of 4-(R)-(−)-1-(3,5-bis-trifluoromethylphenyl)-2-oxopyrrolidine-4-carboxylic acid

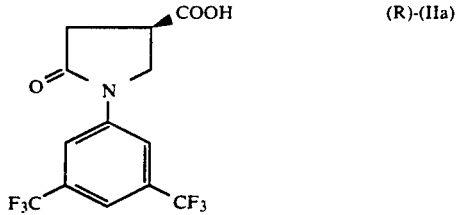

(R)-(IIa)

a) A solution of 331.4 g (2.734 mol) of (R)-(+)-1-phenylethylamine in 500 ml of ethanol is added dropwise with stirring at a temperature of +60° C. to a solution of 932.3 g (2.734 mol) of racemic 1-(3,5-bis-trifluoromethylphenol)-2-oxopyrrolidine-4-carboxylic acid in 6000 ml of ethanol.

The mixture is stirred for 10 hours, during which process it cools to room temperature, and the precipitate which has formed is filtered off and washed with 300 ml of cold ethanol.

b) The precipitate obtained in Example H1a) is dried. Recrystallization from 2500 ml of ethanol gives 369.5 g of a crystalline adduct having a melting point of +189° to +190° C.

c) 355 g of the crystal fraction obtained in Example H1b) are suspended in 1000 ml of water. A pH of 1 to 2 is subsequently established in the suspension using concentrated hydrochloric acid, which results in the formation of a precipitate. The reaction mixture is extracted with 1500 ml of ethyl acetate. The organic phase is subsequently washed with 2N hydrochloric acid and with concentrated sodium chloride solution. Drying over sodium sulfate and evaporation of the solution gives 246 g of 4-(R)-(−)-1-(3,5-bis-trifluoromethylphenyl)-2-oxopyrrolidine-4-carboxylic acid of the formula (R)-(IIa) having a melting point of +127° to 128° C.

EXAMPLE H2

Preparation of 4-(S)-(+)-1-(3,5-trifluoromethylphenyl)-2-oxopyrrolidine-4-carboxylic acid

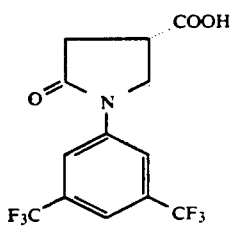
(S)-(IIa)

The filtrate obtained in Example 1a) is evaporated, and the residue is subsequently dissolved in aqueous 2N sodium hydroxide. After the solution has been extracted with dichloromethane, a pH of 1 to 2 is established in the aqueous phase using concentrated hydrochloric acid, which results in the formation of a precipitate. Drying of the precipitate gives 566 g of 4-(S)-(+)-1-(3,5-bis-trifluoromethylphenyl)-2-oxo-pyrrolidine-4-carboxylic acid of the formula (S)-(IIa) having a melting point of +127° to 130° C.

EXAMPLE H3

Preparation of methyl 4-(R)-(−)-1-(3,5-bis-trifluoromethylphenyl)-2-oxopyrrolidine-4-carboxylate

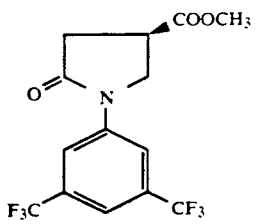
(R)-(IIb)

A solution in 1600 ml of methanol of 246 g of 4-(R)-(−)-1-(3,5-bis-trifluoromethylphenyl)-2-oxopyrrolidine-4-carboxylic acid, the acid prepared as in Example 1, is treated with 20 g of strongly acidic Amberlyst/[reg 15, and the mixture is refluxed for 20 hours. The reaction mixture is subsequently filtered and the filtrate is evaporated. The residue is dissolved in 2000 ml of ethyl acetate, and the solution is washed with 10% aqueous sodium hydrogen carbonate solution and with a saturated sodium chloride solution. After the reaction mixture has been dried over sodium sulfate and active carbon, it is filtered. The filtrate is evaporated to 10% of the original volume, and n-hexane is added, during which process the solution undergoes transition into the two-phase state and the product begins to crystallize.

Filtration gives 200.1 g (41.2% of theory) of methyl 4-(R)-(−)-1-(3,5-bis-trifluoromethylphenyl)-2-oxopyrrolidine-4-carboxylate of the formula (R)-(IIb) having an optical rotation of $a_D^{20}(-)$ 23.0° and a melting point of +54° to +55° C.

EXAMPLE H4

Preparation of methyl 4-(S)-(+)-1-(3,5-bis-trifluoromethylphenyl)-2-oxopyrrolidine-4-carboxylate

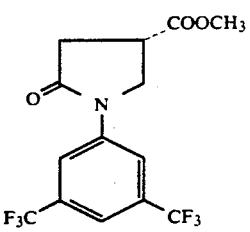
(S)-(IIb)

4-(S)-(+)-1-(3,5-Bis-trifluoromethylphenyl)-2-oxopyrrolidine-4-carboxylic acid, of the formula (S)-(IIa) and prepared as in Example H2, is converted as in Example H3 into methyl 4-(S)-(−)-1-(3,5-bis-trifluoromethylphenyl)-2-oxo-pyrrolidine-4-carboxylate of the formula (S)-(IIb), whose characteristics are a melting point of +54° to +55° C. and an optical rotation of $a_D^{20}(+)$ 23.0°.

EXAMPLE H5

Preparation of methyl 4-(R)-(−)-1-(3,5-bis-trifluoromethylphenyl)-2-thioxopyrrolidine-4-carboxylate (Compound No. 1.01)

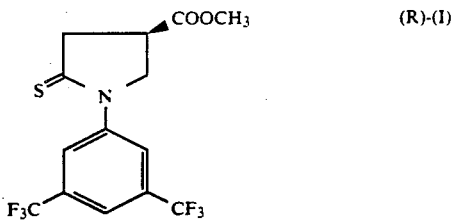
(R)-(I)

A solution of 10.66 g (0.03 mol) of methyl 4-(R)-(−)-1-(3,5-bis-trifluoromethylphenyl)-2-oxopyrrolidine-4-carboxylate, prepared as in Example 3, and of 6.06 g (0.015 mol) of Lawesson's reagent (2,4-bis-(4-methoxyphenyl)-1,3,2,4-dithiadiphosphetane-2,4-dithione) in 70 ml of toluene is heated for 90 minutes at +80° C.

The reaction mixture is subsequently concentrated until a highly-viscous yellow substance is formed. Purification by chromatography over 780 g of silicone dioxide in n-hexane/ethyl acetate (3:1) and recrystallization from a diethyl ether/n-pentane mixture gives, after drying in vacuo at 40° C., 10.18 g (91% of theory) of methyl 4-(R)-(−)-1-(3,5-bis-trifluoromethylphenyl)-2-thioxopyrrolidine-4-carboxylate (compound No. 1.01) in the form of white crystals having a melting point of +83° to +84° C. and an optical rotation of $a_D^{20}(-)$ 13.0°.

EXAMPLE H6

Preparation of methyl 4-(S)-(+)-1-(3,5-bis-trifluoromethylphenyl)-2-thioxopyrrolidine-4-carboxylate (compound No. 1.03)

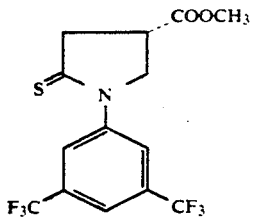
(S)-(I)

Methyl 4-(S)-(+)-1-(3,5-bis-trifluoromethylphenyl)-2-oxopyrrolidine-4-carboxylate, of the formula (S)-(IIb) and prepared as in Example H4, is converted as in Example H5 into methyl 4-(S)-(+)-1-(3,5-bis-trifluoromethylphenyl)-2-thioxopyrrolidine-4-carboxylate of the formula (S)-(I), whose characteristics are a melting point of +85° to +87° C. and an optical rotation of $\alpha_D^{20}$ (+) 13.0°.

EXAMPLE H7

Preparation of racemic methyl 1-(3,5-bis-trifluoromethylphenyl)-2-thioxopyrrolidine-4-carboxylate (compound No. 1.02)

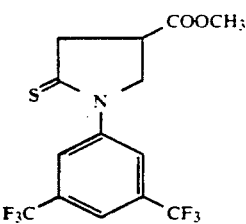
(I)

A solution of 10.66 g (0.03 mol) of methyl 1-(3,5-bis-trifluoromethylphenyl-2-oxopyrrolidine-4-carboxylate, prepared as in Example 3 from racemic 1-(3,5-bis-trifluoromethylphenyl)-2-oxopyrrolidine-4-carboxylic acid is heated to +80° C. for 1 to 2 hours together with 6.06 g of Lawesson's reagent (0.015 mol) in 70 ml of toluene, and the mixture is subsequently evaporated. The crystalline residue is stirred with n-pentane and small amounts of diethyl ether and, at 0° C., placed on a suction filter. Washing of the filter residue with a small amount of n-pentane and drying at +40° C. in vacuo gives 9.19 g (82.5% of theory) of the racemic methyl 1-(3,5-bis-trifluoromethylphenyl)-2-thioxopyrrolidine-4-carboxylate (compound No. 1.02) in the form of white crystals having a melting point of +85° to +87° C.

EXAMPLE H8

Preparation of racemic 1-(3,5-bis-trifluoromethylphenyl)-2-thioxo-pyrrolidine-4-carboxylic acid (compound No. 1.06)

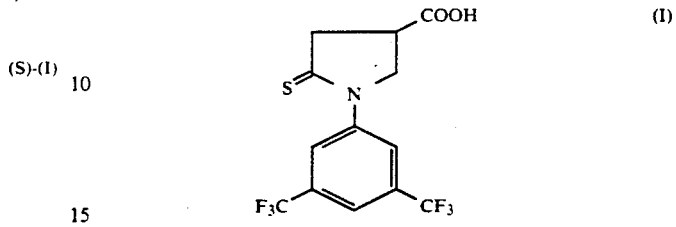
(I)

a) Preparation of tert-butyl 1-(3,5-bis-trifluoromethylphenyl)-2-oxopyrrolidine-4-carboxylate:

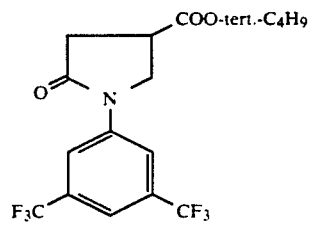

A solution of 3.41 g (0.01 mol) of racemic 1-(3,5-bis-trifluoromethylphenyl)-2-oxo-pyrrolidine-4-carboxylic acid in 50 ml of absolute tetrahydrofuran is cooled to 0° C. and treated with 2.12 ml (0.015 mol) of 1-chloro-1-dimethylamino-2-methyl-1-propene, and the mixture is stirred for 3 hours at 10°-15° C.

After the reaction mixture has been cooled to 0° C., a mixture of 2 ml (0.022 mol) of tert-butanol, 1.6 ml (0.02 mol) of pyridine and 0.24 g (0.002 mol) of 4-dimethylaminopyridine is added.

The mixture is stirred for 12 hours and then extracted with water and dichloroethane, and the organic phase is dried, washed and subsequently evaporated. Chromatographic purification with silica gel/dichloromethane gives 3.76 g (95% of theory) of tert-butyl 1-(3,5-bis-trifluoromethylphenyl)-2-oxopyrrolidine-4-carboxylate in the form of a yellow oil.

b) Preparation of tert-butyl 1-(3,5-bis-trifluoromethylphenyl)-2-thioxopyrrolidine-4-carboxylate (compound No. 1.18):

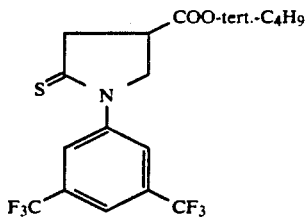

A mixture of 3 g (7.55 mmol) of tert-butyl 1-(3,5-bis-trifluoromethylphenyl)-2-oxopyrrolidine-4-carboxylate, prepared as in Example H8a), is heated at 80° C. with stirring together with 1.53 g (3.77 mmol) of Lawesson's reagent in 20 ml of toluene. After 2 hours, the solution is evaporated, and the resulting residue is purified by chromatography over silica gel/(hexane:ethyl acetate 7:1). 2.82 g (91% of theory) of tert-butyl 1-(3,5-bis-trifluoromethylphenyl)2-thioxopyrrolidine-4-carboxylate (compound No. 1.18) crystallizes from the solution.

c) Preparation of 1-(3,5-bis-trifluoromethylphenyl)-2-thioxopyrrolidine-4-carboxylic acid (compound No. 1.06): 1 g (2.42 mmol) of tert-butyl 1-(3,5-bis-trifluoromethylphenyl)-2-thioxopyrrolidine-4-carboxylate, prepared as in Example H8b), is dissolved in trifluoroacetic acid and the solution is stirred for 2 hours under reduced pressure at room temperature. Excess trifluoroacetic acid is subsequently evaporated. Recrystallization of the resulting residue from diethyl ether/n-pentane gives 0.76 g (89% of theory) of 1-(3,5-bis-trifluoromethylphenyl)-2-thioxopyrrolidine-4-carboxylic acid (compound No. 1.06) in the form of colourless crystals having a melting point of +141° to +142° C.

The following examples of compounds of the formulae I, (R)-IIb and (S)-IIb are representatives of the scope described:

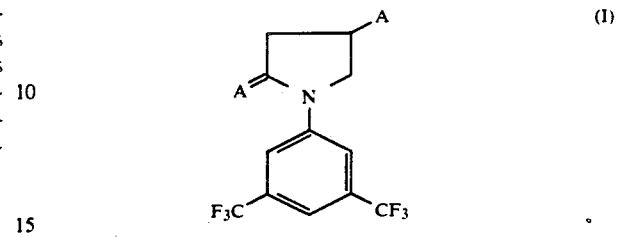

(I)

TABLE 1

| Compound No. | A | Melting point [°C.] | Optical rotation $[\alpha_D^{20}]$ |
|---|---|---|---|
| 1.01 | (R)—COOCH₃ | +83 to +84 | −13° |
| 1.02 | ± —COOCH₃ | +85 to +87 | — |
| 1.03 | (S)—COOCH₃ | +85 to +87 | +13° |
| 1.04 | (R)—COOH | +141 to +142 | −20° |
| 1.05 | (S)—COOH | +140 to +142 | +20° |
| 1.06 | ± —COOH | +141 to +142 | — |
| 1.07 | (R)—COOCH₂CH₃ | | |
| 1.08 | (S)—COOCH₂CH₃ | | |
| 1.09 | ± —COOCH₂CH₃ | | |
| 1.10 | (R)—COO—CH(CH₃)—CH₃ | | |
| 1.11 | (S)—COO—CH(CH₃)—CH₃ | | |
| 1.12 | ± —COO—CH(CH₃)—CH₃ | | |
| 1.13 | (R)—COO—CH₂CH₂CH₂CH₃ | | |
| 1.14 | (S)—COO—CH₂CH₂CH₂CH₃ | | |
| 1.15 | ± —COO—CH₂CH₂CH₂CH₃ | | |
| 1.16 | (R)—COO-tert-C₄H₉ | +60 to +61 | |
| 1.17 | (S)—COO-tert-C₄H₉ | +60 to +62 | |
| 1.18 | ± —COO-tert-C₄H₉ | +96 to +97 | |
| 1.19 | (R)—COOCH₂—CH=CH₂ | +40 to +42 | −10.3° |
| 1.20 | (S)—COOCH₂—CH=CH₂ | | |
| 1.21 | ± —COOCH₂—CH=CH₂ | +42 to +44 | |
| 1.22 | (R)—COOCH₂—C≡CH | +84 to +86 | −10.7° |
| 1.23 | (S)—COOCH₂—C≡CH | | |
| 1.24 | ± —COOCH₂—C≡CH | +47 to +49 | |
| 1.25 | (R)—COOCH₂—CH=CH(CH₃) | | |
| 1.26 | (S)—COOCH₂—CH=CH(CH₃) | | |
| 1.27 | ± —COOCH₂—CH=CH(CH₃) | | |
| 1.28 | (R)—COOCH₂—C≡C—CH₃ | | |
| 1.29 | (S)—COOCH₂—C≡C—CH₃ | | |
| 1.30 | ± —COOCH₂—C≡C—CH₃ | | |
| 1.31 | (R)—COCl | | |
| 1.32 | (S)—COCl | | |
| 1.33 | ± —COCl | | |
| 1.34 | (R)—COSCH₃ | | |
| 1.35 | (S)—COSCH₃ | | |
| 1.36 | ± —COSCH₃ | +108 ot +110 | |
| 1.37 | (R)—COS-n-C₄H₉ | oil | −10.3° |
| 1.38 | (S)—COS-n-C₄H₉ | | |
| 1.39 | ± —COS-n-C₄H₉ | +62 to +63 | |

TABLE 1-continued

| Compound No. | A | Melting point [°C.] | Optical rotation $[\alpha_D^{20}]$ |
|---|---|---|---|
| 1.40 | (R)—CON(CH₃)₂ | | |
| 1.41 | (S)—CON(CH₃)₂ | | |
| 1.42 | ± —CON(CH₃)₂ | +120 to +122 | |
| 1.43 | (R)—COO⁻Na⁺ | | |
| 1.44 | (S)—COO⁻Na⁺ | | |
| 1.45 | ± —COO⁻Na⁺ | +248 to +250 | |
| 1.46 | [(R)—COO⁻]₂Ca²⁺ | | |
| 1.47 | [(S)—COO⁻]₂Ca²⁺ | | |
| 1.48 | [± —COO⁻]₂Ca²⁺ | | |
| 1.49 | (R)—COO⁻⁺NH(C₄H₉)₃ | | |
| 1.50 | (S)—COO⁻⁺NH(C₄H₉)₃ | | |
| 1.51 | ± —COO⁻⁺NH(C₄H₉)₃ | oil | |
| 1.52 | (R)—COO⁻⁺NH₄ | | |
| 1.53 | (S)—COO⁻⁺NH₄ | | |
| 1.54 | ± —COO⁻⁺NH₄ | | |
| 1.55 | (R)—CO—N(2-methylpiperidinyl) | | |
| 1.56 | (S)—CO—N(2-methylpiperidinyl) | | |
| 1.57 | ± —CO—N(2-methylpiperidinyl) | | |
| 1.58 | (R)—CO—NH—cyclopropyl | | |
| 1.59 | (S)—CO—NH—cyclopropyl | | |
| 1.60 | ± —CO—NH—cyclopropyl | +172 to +174 | |
| 1.61 | ± —CO—N(morpholinyl) | +120 to +122 | |

TABLE 2

Intermediates of the formula (R)-(IIb)

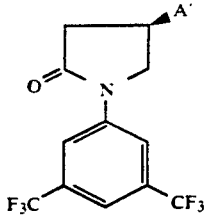

| Compound No. | A' | Melting point [°C.] | Optical rotation $[\alpha_D^{20}]$ |
|---|---|---|---|
| 2.01 | —COOCH₃ | +54 to +55 | −23° |
| 2.02 | —COOCH₂CH₃ | | |
| 2.03 | —COO—CH(CH₃)—CH₃ | | |
| 2.04 | —COO—CH₂CH₂CH₂CH₃ | | |
| 2.05 | —COO-tert-C₄H₉ | oil | |
| 2.06 | —COO—CH(CH₃)—CH₂—CH₃ | | |

TABLE 3

Intermediates of the formula (S)-(IIb)

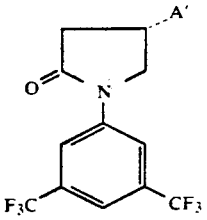

| Compound No. | A' | Melting point [°C.] | Optical rotation $[\alpha_D^{20}]$ |
|---|---|---|---|
| 3.01 | —COOCH₃ | +54 to +55 | +23° |
| 3.02 | —COOCH₂CH₃ | | |
| 3.03 | —COO—CH(CH₃)—CH₃ | | |
| 3.04 | —COO—CH₂CH₂CH₂CH₃ | | |
| 3.05 | —COO-tert-C₄H₉ | oil | |
| 3.06 | —COO—CH(CH₃)—CH₂—CH₃ | | |

BIOLOGICAL EXAMPLES

The effectiveness of the compounds of the formula I according to the invention was tested as follows:

EXAMPLE B1

Safening Action in Maize (Tank Mix)

To test for safening action, maize seeds cv. Blizzard were grown in soil in 9×9 cm pots. The plants were grown in the greenhouse under adapted temperature and light conditions. The plants were watered and fed as required.

The safener substance (400 g of active compound/ha) was applied after the plants emerged (post-emergence) as a tank mix together with the herbicide, 550 liters of water being used per hectare.

To determine the safening action (protective action), the general damage (phytotoxicity) to the plants was scored 14 days after application (0% phytotoxicity=no damage, like untreated control; 100% phytotoxicity=-total destruction). The protective action in [%], which is listed in Table 2, is calculated from the difference of the phytotoxicity of the herbicide treatment alone and of the combination of herbicide plus safener.

The results for the herbicide of the formula IIIa below

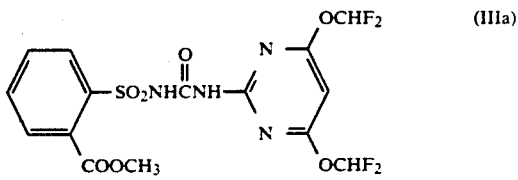
(IIIa)

N-(2-methoxycarbonylphenylsulfonyl)-N'-(4,6-bis-difluoromethoxypyrimidin-2-yl)-urea and the safeners methyl 1-(3,5-bis-trifluoromethylphenyl)-2-thioxopyrrolidine-4-carboxylate (compound No. 1.02) and methyl 4-(R)-1-(3,5-bis-trifluoromethylphenyl)-2-thioxopyrrolidine-4-carboxylate (compound No. 1.01) are listed in Table 2.

| Herbicide of the formula IIIa Application rate 75 g/ha | Protective action in % |
|---|---|
| Safener No. 1.01 | 12% |
| Safener No. 1.02 | 12% |

EXAMPLE B2

Safening Action in Rice (Tank Mix)

To test for safening action, rice seeds (cultivar S-201) are grown in boggy soil in 9×9 cm pots. The plants were grown in the greenhouse under adapted temperature and light conditions. The plants were watered and fed as required.

The safener substance (250 g of active compound/ha) was applied before the plants emerged (pre-emergence) as a tank mix together with the herbicide, 550 liters of water being used per hectare. The rice seeds are soaked for about 40 hours before sowing.

To determine the safening action (protective action), the general damage (phytotoxicity) to the plants was scored 14 days after application (0% phytotoxicity=no damage, like untreated control; 100% phytotoxicity=-total destruction). The protective action in % is calculated from the difference of the phytotoxicity of the herbicide treatment alone and of the combination of herbicide plus safener.

The results for the herbicide N-chloroacetyl-N-(2-n-propoxyethyl)-2,6-diethylaniline, of the formula IVa,

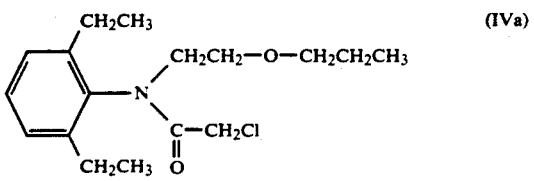
(IVa)

and the safeners No. 1.01 and No. 1.02 are listed in Table 3.

TABLE 3

| Herbicide of the formula IVa Application rate 1.5 kg/ha | Protective action in % |
|---|---|
| Safener No. 1.01 | 38% |
| Safener No. 1.02 | 25% |

EXAMPLE B3

Inhibition of Growth in Tropical Leguminous Cover Crops

The plants (for example Centrosema pubescens or Psophocarpus palustris) are propagated by cuttings in 4 cm peat pots with field soil (45%), peat (45%) and zonolite (10%). They are grown in the greenhouse at a day temperature of 27° C. and a night temperature of 23° C. The plants are illuminated for at least 14 hours/day at an intensity of at least 7000 lux.

About 50 days after planting the cuttings, they are repotted in 13 cm pots, 4-5 plants/pot. After a further 60 days, the plants are cut back to a height of about 15 cm, and subjected to the application treatment. In this treatment, they are sprayed with 0.3 to 3 kg of active substance/ha (formulated, as a rule, as a 25% concentration) in an aqueous spray liquor. The amount of water applied is about 200 l/ha.

The experiment is evaluated 4 weeks after the application. In this evaluation, the additional growth is scored and weighed in comparison with the control, and the phytotoxicity is rated. In this experiment, the plants treated with the active substances from Table 1 show a marked reduction of additional growth without inflicting damage on the experimental plants.

EXAMPLE B4

Growth Regulation in Soya Beans

The plants (for example cultivar Williams) are sown in 11 cm clay pots with field soil (45%), peat (45%) and zonolite (10%), and grown in a growth cabinet at a day temperature of 24° C. and a night temperature of 19° C. The plants are illuminated for a period of 16 hours per day at an intensity of about 2900 lux.

About 24 days after sowing, repotting into 18 cm pots is effected, 2 plants per pot. After a further 12 days and in the stage where 5-6 trifoliate leaves have appeared, up to 100 g of active substance/ha is applied to the plants, the formulation being, as a rule, 25% concentration and in aqueous spray liquor. The amount of water applied is about 200 l/ha.

The experiment is evaluated about 4 weeks after the application. In comparison with the untreated control plants, the active substances from Table 1 according to the invention result in a markedly reduced growth without phytotoxicity.

EXAMPLE B5

Selective Growth Inhibition of Oil Seed Rape and Clover in Maize

The compounds of Table 1 are highly suitable for selectively and strongly inhibiting cover crops in a maize crop and therefore preventing the undersown crop from competing for water and nutrients, while simultaneously maintaining the agronomically desired effects of the undersown crop, such as protection from erosion, nitrogen fixation and reduction of soil compaction. This is shown in Table 4 for the crop combinations maize/white clover and maize/oil seed rape, using compound No. 1.01 as an example:

"Blizzard" maize is sown in 15 cm pots with field soil and grown for 15 days in the greenhouse at day/night temperatures of 22°/19° C. and an illumination period of at least 13.5 hours/day in the case of post-emergence application, pre-emergence application being carried out one day after sowing.

"Bienvenue" oil seed rape is sown in 15 cm pots with field soil, and grown for 7 days at day/night temperatures of 22°/19° C., then for 17 days at 10°/5° C. and then for 7 days at 15°/10° C. until the application was effected.

"Ladino" white clover is grown in 15 cm pots with a mixture of field soil (60%), peat substrate (30%) and zonolite (10%) for 40 days at day/night temperatures of 21°/18° C. and a minimum illumination period of 13.5 hours.

All crops are fed and watered as required, the compound No. 1.01 (formulated in a 25% concentration) is applied in 200 l of water/ha and at application rates of 30 to 500 g/ha. 28 days after application, the height of the additional growth is measured, and the action is represented in per cent growth inhibition in comparison with the untreated control. 100% action denotes no additional growth at all, 0% action denotes growth as in the untreated control.

The following results were obtained:

TABLE 4

| Dosage g/ha | Maize pre-em. % | Maize post-em. % | Oil seed rape post-em. % | White clover post-em. % |
|---|---|---|---|---|
| Control | 0 | 0 | 0 | 0 |
| 30 | — | 0 | — | — |
| 60 | 0 | 0 | 59 | 25 |
| 125 | 0 | 0 | 76 | 55 |
| 250 | 0 | 0 | 100 | 85 |
| 500 | 0 | 0 | 100 | 100 |

The results show that it is possible to selectively inhibit dicotyledon undersown crops in maize by using the compounds of Table 1. With regard to maize, the application can be effected pre-emergence or post-emergence.

We claim:

1. A 1-(3,5-bis-trifluoromethylphenyl)-2-thioxopyrrolidine-4-carboxylic acid derivative of formula I (I)

where A is $-COOR_1$, $-COSR_1$, $-COO^{\ominus}M^{\oplus}$, $-CONR_2R_3$ or $-COCl$; $R_1$ is hydrogen, $C_1$-$C_4$alkyl, $C_2$-$C_6$alkenyl or $C_2$-$C_6$alkynyl; $R_2$ and $R_3$ independently of one another are hydrogen, $C_1$-$C_4$alkyl or $C_3$-$C_7$cycloalkyl; or $R_2$ and $R_3$ together with the nitrogen atom to which they are bonded are pyrrolidine, piperazine, 2-methylpiperazine, piperidine and morpholine which is unsubstituted or up to trisubstituted by $C_1$-$C_4$alkyl; and $M^{\oplus}$ is the equivalent of an alkali metal cation or an alkaline earth metal cation or $HN^{\oplus}(R_2)_3$, and an isomer thereof in optically pure or enriched form.

2. A compound of the formula I according to claim 1, wherein A is —COOR₁ or —COO⊖M⊕.

3. A compound of the formula (R)-I

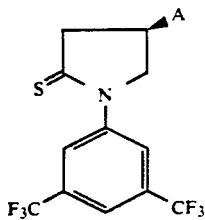

where A is as defined in claim 1, in optically pure or enriched form.

4. A compound according to claim 1, of the formula (S)-I

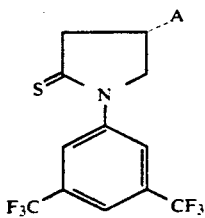

where A is as defined in formula I, in optically pure or enriched form.

5. A compound of the formula (R)-I according to claim 3, wherein A is —COOR₁ or —COO⊖M⊕.

6. A compound of the formula (S)-I according to claim 4, wherein A is —COOR₁ or —COO⊖M⊕.

7. 4-(R)-(−)-1-(3,5-bis-trifluoromethylphenyl)-2-thioxopyrrolidine-4-carboxylic acid according to claim 1.

8. Methyl 4-(R)-(−)-1-(3,5-bis-trifluoromethylphenyl)-2-thioxopyrrolidine-4-carboxylate according to claim 1.

9. 4-(S)-(+)-1-(3,5-bis-trifluoromethylphenyl)-2-thioxopyrrolidine-4-carboxylic acid according to claim 1.

10. Methyl 4-(S)-(+)-1-(3,5-bis-trifluoromethylphenyl)-2-thioxopyrrolidine-4-carboxylate according to claim 1.

11. 1-(3,5-Bis-trifluoromethylphenyl)-2-thioxopyrrolidine-4-carboxylic acid according to claim 1.

12. Methyl 1-(3,5-Bis-trifluoromethylphenyl)-2-thioxopyrrolidine-4-carboxylate according to claim 1.

13. A method of protecting crop plants against the crop-plant damaging action of herbicides, which comprises treating the crop plant, its environment, parts of the crop plant or its seeds or cuttings before, during or after the application of the herbicide, with an antagonistically effective amount of a 1-(3,5-bis-trifluoromethylphenyl)-2-thioxopyrrolidine-4-carboxylic acid derivative of claim 1.

14. A method according to claim 13, wherein A is —COOR₁ or —COO⊖M⊕.

15. A method according to claim 13 or 14 against the damaging action of chloroacetanilide herbicides or sulfonylurea herbicides.

16. A method according to claim 15 in a maize, sorghum or rice crop.

17. A method according to claim 13 or 14 against the damaging action of a herbicidal sulfonylurea derivative of formula III

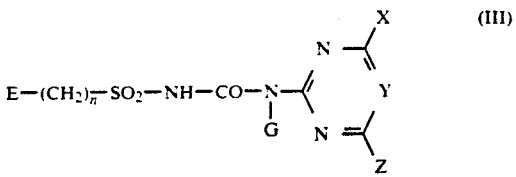

where E is a group

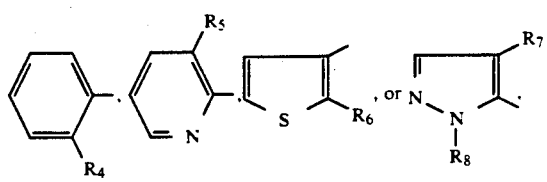

n is the number zero or one. G is hydrogen or methyl, X is methoxy, ethoxy, difluoromethoxy, methyl or chlorine, Y is CH or N, Z is methoxy, methyl, difluoromethoxy, cyclopropyl or methylamino, R₄ is C₂-C₅alkoxyalkoxy, C₁-C₄haloalkoxy, C₁-C₄haloalkylthio, C₂-C₄haloalkenyl, chlorine or C₁-C₄alkoxycarbonyl, R₅ is trifluoromethyl or di(C₁-C₄alkyl)carbamoyl, R₆ is C₁-C₄alkoxycarbonyl, R₇ is C₁-C₄alkoxycarbonyl, and R₈ is C₁-C₄alkyl.

18. A method according to claim 17 against the damaging action of

N'-(3-trifluoromethylpyridin-2-ylsulfonyl)-N'-(4,6-dimethoxypyrimidin-2-yl)-urea, N-(3-dimethylcarbamoylpyridin-2-ylsulfonyl)-N'-(4,6-dimethoxypyrimidin-2-yl)-urea, N-(1-methyl-4-ethoxycarbonylpyrazol-2-ylsulfonyl)-N'-(4,6-dimethoxypyrimidin-2-yl)-urea, N-(2-methoxycarbonylthien-3-ylsulfonyl)-N'-(4-methoxy-6-methyl-1,3,5-triazin-2-yl)-urea, N-(2-methoxycarbonylbenzylsulfonyl)-N'-(4,6-dimethoxypyrimidin-2-yl)-urea, N-(2-methoxycarbonylphenylsulfonyl)-N'-(4,6-bis-difluoromethoxy-pyrimidin-2-yl)-urea, N-(2-methoxycarbonylphenylsulfonyl)-N'-(4-ethoxy-6-methylamino-1,3,5-triazin-2-yl)-urea, N-(2-methoxycarbonylphenylsulfonyl)-N'-(4-methoxy-6-methyl-1,3,5-triazin-2-yl)-urea, N-(2-ethoxycarbonylphenylsulfonyl)-N'-(4-chloro-6-methoxypyrimidin-2-yl)-urea, N-(2-methoxycarbonylphenylsulfonyl)-N'-(4-methoxy-6-methyl-1,3,5-triazin-2-yl)-N'-methylurea, N-(2-methoxycarbonylphenylsulfonyl)-N'-(4,6-dimethoxypyrimidin-2-yl)-urea, N-(2-chlorophenylsulfonyl)-N'-(4-methoxy-6-methyl-1,3,5-triazin-2-yl)-urea, N-[2-(2-chloroethoxy)-phenylsulfonyl]-N'-(4-methoxy-6-methyl-1,3,5-triazin-2-yl)-urea and N-[2-(2-methoxyethoxy)-phenylsulfonyl]-N'-(4,6-dimethoxy-1,3,5-triazin-2-yl)-urea.

19. A method according to claim 13 or 14 against the damaging action of a herbicidal haloacetanilide of formula IV

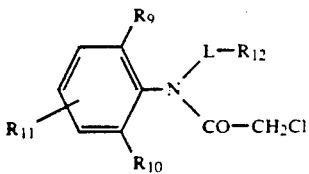

where L is a $C_1$-$C_4$alkylene bridge, $R_9$, $R_{10}$ and $R_{11}$ independently of one another are hydrogen, halogen, $C_1$-$C_4$alkyl, $C_1$-$C_4$alkoxy, $C_1$-$C_4$haloalkyl, $C_2$-$C_5$alkoxyalkyl or $C_2$-$C_5$alkylthioalkyl, and $R_{12}$ is $C_1$-$C_4$alkoxy, —COOH, $C_1$-$C_4$alkoxycarbonyl, —CONH$_2$, hydrogen, $C_1$-$C_4$alkylcarbamoyl, di-$C_1$-$C_4$alkylcarbamoyl, cyano, $C_1$-$C_4$alkylcarbonyl, substituted or unsubstituted benzoyl, substituted or unsubstituted furyl, substituted or unsubstituted thienyl, substituted or unsubstituted pyrrolyl, substituted or unsubstituted pyrazolyl, substituted or unsubstituted 1,3,4-oxadiazol-2-yl, substituted or unsubstituted 1,3,4-thiadiazol-2-yl, substituted or unsubstituted dioxolanyl, substituted or unsubstituted dioxanyl, substituted or unsubstituted 1,3,4-triazol-2-yl or substituted or unsubstituted tetrahydrofuryl.

20. A method according to claim 19 against the damaging action of a herbicidal haloacetanilide of the formula IV

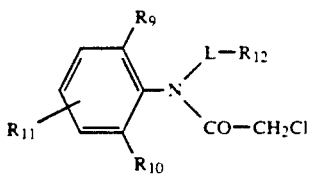

where L is a $C_1$-$C_4$alkylene bridge, $R_9$, $R_{10}$ and $R_{11}$ independently of one another are hydrogen, halogen, $C_1$-$C_4$alkyl, $C_1$-$C_4$alkoxy, $C_1$-$C_4$haloalkyl, $C_2$-$C_5$alkoxyalkyl or $C_2$-$C_5$alkylthioalkyl, and $R_{12}$ is $C_1$-$C_4$alkoxy, —COOH, $C_1$-$C_4$alkoxycarbonyl, —CONH$_2$, hydrogen, $C_1$-$C_4$alkylcarbamoyl, di-$C_1$-$C_4$alkylcarbamoyl, cyano or $C_1$-$C_4$alkylcarbonyl.

21. A method according to claim 19 against the damaging action of

N-ethoxymethyl-N-chloroacetyl-2-ethyl-6-methylaniline,
N-chloroacetyl-N-methoxymethyl-2,6-diethylaniline,
N-chloroacetyl-N-(2-methoxyethyl)-2,6-dimethylaniline,
N-chloroacetyl-N-(2-n-propoxyethyl)-2,6-dimethylaniline,
N-chloroacetyl-N-(2-isopropoxyethyl)-2,6-dimethylaniline,
N-chloroacetyl-N-(2-methoxyethyl)-2-ethyl-6-methylaniline,
N-chloroacetyl-N-(methoxyethyl)-2,6-diethylaniline,
N-(2-ethoxyethyl)-N-chloracetyl-2-ethyl-6-methylaniline,
N-chloroacetyl-N-(2-methoxy-1-methylethyl)-2-methylaniline,
N-chloroacetyl-N-(2-methoxy-1-methylethyl)-2,6-dimethylaniline,
N-chloroacetyl-N-(2-methoxy-1-methylethyl)-2,6-diethylaniline,
N-chloroacetyl-N-(2-methoxy-1-methylethyl)-2-ethyl-6-methylaniline,
N-(2-ethoxyethyl)-N-chloroacetyl-2,6-diethylaniline,
N-chloroacetyl-N-(2-n-propoxyethyl)-2-ethyl-6-methylaniline,
N-chloroacetyl-N-(2-n-propoxyethyl)-2,6-diethylaniline,
N-chloroacetyl-N-(2-isopropoxyethyl)-2-ethyl-6-methylaniline,
N-ethoxycarbonylmethyl-N-chloroacetyl-2,6-dimethylaniline,
N-ethoxycarbonylmethyl-N-chloroacetyl-2,6-diethylaniline,
N-chloroacetyl-N-methoxycarbonylmethyl-2,6-dimethylaniline,
N-chloroacetyl-N-(2,2-diethoxyethyl)-2,6-dimethylaniline,
N-chloroacetyl-N-(2-methoxy-1-methylethyl)-2,3-dimethylaniline,
N-(2-ethoxyethyl)-N-chloroacetyl-2-methylaniline,
N-chloroacetyl-N-(2-methoxyethyl)-2-methylaniline,
N-chloroacetyl-N-(2-methoxy-2-methylethyl)-2,6-dimethylaniline,
N-(2-ethoxy-2-methylethyl)-N-chloroacetyl-2-ethyl-6-methylaniline,
N-chloroacetyl-N-(1-ethyl-1-methoxyethyl)-2,6-dimethylaniline,
N-chloroacetyl-N-(2-methoxyethyl)-2-methoxy-6-methylaniline,
N-n-butoxymethyl-N-chloroacetyl-2-tert-butylaniline,
N-chloroacetyl-N-(2-ethoxyethyl-2-methylethyl)-2,6-dimethylaniline,
N-chloroacetyl-N-(2-methoxyethyl)-2-chloro-6-methylaniline,
N-(2-ethoxyethyl)-N-chloroacetyl-2-chloro-6-methylaniline,
N-(2-ethoxyethyl)-N-chloroacetyl-2,3,6-trimethylaniline,
N-chloroacetyl-1-(2-methoxyethyl)-2,3,6-trimethylaniline,
N-chloroacetyl-N-cyanomethyl-2,6-dimethylaniline,
N-chloroacetyl-N-(1,3-dioxolan-2-ylmethyl)-2,6-dimethylaniline,
N-chloroacetyl-N-(1,3-dioxolan-2-ylmethyl)-2-ethyl-6-methylaniline,
N-chloroacetyl-N-(1,3-dioxan-2-ylmethyl)-2-ethyl-6-methylaniline,
N-chloroacetyl-N-(2-furylmethyl)-2,6-dimethylaniline,
N-chloroacetyl-N-(2-furylmethyl)-2-ethyl-6-methylaniline,
N-chloroacetyl-N-(2-tetrahydrofurylmethyl)-2,6-dimethylaniline,
N-chloroacetyl-N-(N,N-dimethylcarbamoylmethyl)-2,6-dimethylaniline,
N-(n-butoxymethyl)-N-chloroacetyl-2,6-diethylaniline,
N-(2-n-butoxyethyl)-N-chloroacetyl-2,6-diethylaniline,
N-chloroacetyl-N-(2-methoxy-1,2-dimethylethyl)-2,6-dimethylaniline,
N-chloroacetyl-N-isopropyl-2,3-dimethylaniline,
N-chloroacetyl-N-isopropyl-2-chloroaniline,
N-chloroacetyl-N-(1H-pyrazol-1-ylmethyl)-2,6-dimethylaniline,
N-chloroacetyl-N-(1H-pyrazol-1-ylmethyl)-2-ethyl-6-methylaniline,
N-chloroacetyl-N-(1H-1,2,4-triazol-1-ylmethyl)-2,6-dimethylaniline, N-chloroacetyl-N-(1H-1,2,4-triazol-1-ylmethyl)-2,6-diethylaniline, N-benzoylmethyl-N-chloroacetyl-2,6-diethylaniline, N-benzoylmethyl-N-chloroacetyl-2-ethyl-6-methylaniline, N-chloroacetyl-N-(5-methyl-1,3,4-oxadiazol-2-yl)-2,6-diethylaniline, N-chloroacetyl-N-(5-methyl-1,3,4-oxadiazol-2-yl)-2-ethyl-6-methylaniline, N-chloroacetyl-N-(5-methyl-1,3,4-oxadiazol-2-yl)-2-tert-butylaniline, N-chloroacetyl-N-(4-chlorobenzoylmethyl)-2,6-dimethylaniline and N-chloroacetyl-N-(1-methyl-5-methylthio-1,3,4-triazol-2-ylmethyl)-2,6-diethylaniline.

22. A method according to claim 13 or 14 against the damaging action of N-chloroacetyl-N-(2-n-propoxyethyl)-2,6-diethylaniline.

23. A herbicidal agent containing a herbicide and an amount, antagonizing the crop-plant damaging action, of 1-(3,5-bis-trifluoromethylphenyl)-2-thioxopyrrolidine-4-carboxylic acid derivatives of the formula I

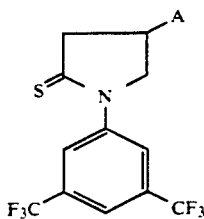

where A is as defined in claim 1, and, if desired, other auxiliaries and/or carriers.

24. A herbicidal agent according to claim 23, wherein A is as defined in claim 2.

25. A herbicidal agent according to claim 23 or 24, containing a herbicide from the group of the chloroacetanilides or sulfonylureas.

26. Crop-plant seeds which have been treated with an antagonistically effective amount of a herbicide antagonist selected from the group consisting of 1-(3,5-bis-trifluoromethylphenyl)-2-thioxopyrrolidine-4-carboxylic acid derivatives and isomers thereof in optically pure or enriched form of formula I

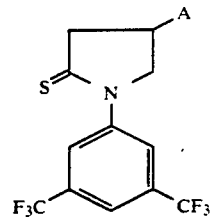

where A is $-COOR_1$, $-COSR_1$, $-COO^{\ominus}M^{\oplus}$, $-CONR_2R_3$ or $-COCl$; $R_1$ is hydrogen, $C_1$-$C_4$alkyl, $C_2$-$C_6$alkenyl or $C_2$-$C_6$alkynyl; $R_2$ and $R_3$ independently of one another are hydrogen, $C_1$-$C_4$alkyl or $C_3$-$C_7$cycloalkyl; or $R_2$ and $R_3$ together with the nitrogen atom to which they are bonded are pyrrolidine, piperazine, 2-methylpiperazine, piperidine and morpholine which is unsubstituted or up to trisubstituted by $C_1$-$C_4$alkyl; and $M^{\oplus}$ is the equivalent of an alkali metal cation or an alkaline earth metal cation or $HN^{\oplus}(R_2)_3$.

27. Treated seeds of claim 26 wherein A is $-COOR_1$ or $-COO^{\ominus}M^{\oplus}$.

28. The treated seeds of claims 26 or 27 selected from the group consisting of sorghum, rice or maize seeds.

29. A plant-growth inhibiting agent, containing, besides carriers and/or other adjuvants, at least one pyrrolidinecarboxylic acid derivative of the formula I as active substance, according to claim 1.

30. An agent according to claim 29, containing between 0.1% and 95% of active substance of the formula I according to claim 1.

31. A method for inhibiting plant growth, which comprises applying an active substance of the formula I, according to claim 1, or an agent containing this active substance, according to claim 29, in an effective amount to the plants or their environment.

32. A method according to claim 31, wherein an amount of active substance of between 0.01 and 10 kg is applied per hectare.

33. A method for influencing plant growth with the aim of increasing the yield, which comprises applying an active substance of the formula I, according to claim 1, or an agent containing this active substance, according to claim 29, in an effective amount to the plants or their environment.

* * * * *